(12) United States Patent
Saphier (10) Patent No.: US 10,406,317 B2
(45) Date of Patent: Sep. 10, 2019

(54) MICROCATHETER SYSTEM AND METHOD THEREFOR

(71) Applicant: Paul Saphier, Morristown, NJ (US)

(72) Inventor: Paul Saphier, Morristown, NJ (US)

(73) Assignee: Paul Saphier, Morristown, NJ (US)

( * ) Notice: Subject to any disclaimer, the term of this patent is extended or adjusted under 35 U.S.C. 154(b) by 378 days.

(21) Appl. No.: 15/385,211

(22) Filed: Dec. 20, 2016

(65) Prior Publication Data

US 2017/0100563 A1 Apr. 13, 2017

Related U.S. Application Data

(63) Continuation-in-part of application No. 14/806,757, filed on Jul. 23, 2015, now Pat. No. 9,844,642.

(60) Provisional application No. 62/159,543, filed on May 11, 2015, provisional application No. 62/270,386, filed on Dec. 21, 2015.

(51) Int. Cl.
  *A61M 25/00* (2006.01)
  *A61M 25/16* (2006.01)
  *A61M 25/18* (2006.01)
  *A61M 39/10* (2006.01)

(52) U.S. Cl.
  CPC ...... *A61M 25/0023* (2013.01); *A61M 25/005* (2013.01); *A61M 25/007* (2013.01); *A61M 25/0097* (2013.01); *A61M 39/10* (2013.01); *A61M 2025/0042* (2013.01); *A61M 2039/1083* (2013.01); *A61M 2039/1088* (2013.01); *A61M 2205/0266* (2013.01); *A61M 2205/32* (2013.01); *A61M 2210/12* (2013.01)

(58) Field of Classification Search
  CPC .. A61M 2025/0042; A61M 2039/1083; A61M 2039/1088; A61M 2205/0266; A61M 2205/32; A61M 2210/12; A61M 25/0023; A61M 25/005; A61M 39/10
  USPC ........................................................ 604/526
  See application file for complete search history.

(56) References Cited

U.S. PATENT DOCUMENTS

| | | | | |
|---|---|---|---|---|
| 3,552,778 A | * | 1/1971 | Muller | A61M 16/08 285/127.1 |
| 5,851,203 A | | 12/1998 | Van Muiden | |
| 2004/0153049 A1 | * | 8/2004 | Hewitt | A61M 25/0012 604/527 |
| 2008/0284167 A1 | * | 11/2008 | Lim | A61M 39/10 285/382 |
| 2010/0049165 A1 | | 2/2010 | Sutherland et al. | |

FOREIGN PATENT DOCUMENTS

EP 2444116 A1 4/2012

* cited by examiner

*Primary Examiner* — Jason E Flick
(74) *Attorney, Agent, or Firm* — Duane Morris LLP (57) ABSTRACT

A microcatheter system is disclosed which may include a microcatheter, one or more microcatheter extensions, and/or a microcatheter hub. In an embodiment, the microcatheter has a plurality of zones where the outside diameter of each zone from the distal to the proximal end has an outside diameter that is the same as or greater than the previous zone while the inside diameter is constant throughout the microcatheter length. In a further embodiment, a unique joining mechanism is employed for coupling a microcatheter to a microcatheter extension or to a microcatheter hub. In a further embodiment, the microcatheter has at least one perforation along a sidewall of the microcatheter.

20 Claims, 5 Drawing Sheets

MICROCATHETER SYSTEM AND METHOD THEREFOR

RELATED APPLICATION

The present application is a continuation-in-part of and claims priority benefit of U.S. application Ser. No. 14/806,757, filed 23 Jul. 2015 and entitled "Microcatheter System", which claims priority benefit of U.S. Provisional Application No. 62/159,543, filed 11 May 2015 and entitled "Microcatheter System". The present application also claims priority benefit of U.S. Provisional Application No. 62/270,386, filed 21 Dec. 2015 and entitled "Microcatheter System". The entirety of each of the above-listed applications are hereby incorporated herein by reference.

FIELD

This disclosure relates to a microcatheter system, including a system having a microcatheter and a microcatheter extension and/or a microcatheter hub, where a unique joining mechanism couples two of the components together.

BACKGROUND

Microcatheters, including endovascular and neuroendovascular microcatheters, are generally microtubes inserted into the body through a blood vessel such as the femoral artery and have a variety of uses. Typically, microcatheters have a distal and a proximal end, where at or close to the distal end a marker band is employed for visualization of microcatheter positioning during in vivo use. The marker band typically comprises a metal or metal alloy ring such as platinum, nitinol and/or gold rings which can be visualized via fluoroscopy.

Microcatheters are typically used to embolize the neurovasculature such as in treating arteriovenous malformations (AVMs), aneurysms, and the like in a relatively non-invasive manner. Microcatheters with sufficient flexibility and size for applications in small tortuous vessels have been developed but typically require the continuous use of a guide catheter.

A wide variety of commercially available microcatheters have been developed for insertion in the vascular system for a number of diagnostic or therapeutic applications. Certain applications, however, require a small diameter and very flexible catheter to access small tortuous vessels in situ. Guide catheters of larger diameter are usually employed to act as a conduit to help support microcatheter access. One problem associated with the removal of guide catheters is the increased risk associated with thromboembolic and vascular wall injury complications. It would be beneficial to have a microcatheter system that can remain in situ at a desired vascular location without the need for a larger diameter guide catheter to also remain in situ.

SUMMARY

An aspect of at least one of the embodiments described herein includes the realization that it is advantageous to provide microcatheters which can remain in situ at a desired vascular location without the need for a larger diameter guide catheter to also remain in situ. It is further advantageous to provide microcatheters which easily are extensible and safely detachable/attachable in situ microcatheters with a unique joining mechanism which couples, for example, a microcatheter with a microcatheter extension without requiring an increase in the diameter of the microcatheter system at the joint. The unique joining mechanism is sometimes referred to herein as an internal Luer lock mechanism. The matching parts (male (probe) and female (receptacle) portions as described in further detail below) of the unique joining mechanism may be secured together by, for example, press fitting so that the matching parts remain in place due to friction.

According to one aspect of the present disclosure, a microcatheter system is described which includes a microcatheter having a distal end and a proximal end, wherein an internal diameter is constant throughout, and wherein the microcatheter includes a plurality of zones each zone having an outside diameter that is different from the outside diameter of each of the other zones in the plurality of zones; wherein the proximal end of the microcatheter is configured as a first receptacle for receiving a first probe for connecting a first microcatheter extension or a microcatheter hub to the microcatheter, and wherein an outside diameter of the first receptacle is no greater than a largest diameter of the zones in the plurality of zones; and the first microcatheter extension having a distal end and a proximal end, wherein an internal diameter is constant throughout, and wherein an outside diameter is constant throughout, and wherein the distal end of the first microcatheter extension is configured as the first probe to be received by the first receptacle of the proximal end of the microcatheter, and wherein an outside diameter of the first probe is less than an internal diameter of the first receptacle, wherein the internal diameter of the microcatheter is the same as the internal diameter of the first microcatheter extension, and wherein an outside diameter of the first microcatheter extension is the same as the outside diameter of the largest diameter of the zones in the plurality of zones.

According to another aspect of the present disclosure, a microcatheter system is described which includes a microcatheter having a distal end and a proximal end, wherein an internal diameter is constant throughout, and wherein the microcatheter includes a plurality of zones each zone having an outside diameter that is different from the outside diameter of each of the other zones in the plurality of zones; wherein the proximal end of the microcatheter is configured as a first probe for connecting to a first receptacle for connecting a first microcatheter extension or a microcatheter hub to the microcatheter, and wherein an outside diameter of the first probe is less than an internal diameter of the first receptacle; and the first microcatheter extension having a distal end and a proximal end, wherein an internal diameter is constant throughout, and wherein an outside diameter is constant throughout, and wherein the distal end of the first microcatheter extension is configured as the first receptacle to receive the first probe of the proximal end of the microcatheter, and wherein an outside diameter of the first receptacle is no greater than a largest diameter of the zones in the plurality of zones, wherein the internal diameter of the microcatheter is the same as the internal diameter of the first microcatheter extension, and wherein an outside diameter of the first microcatheter extension is the same as the outside diameter of the largest diameter of the zones in the plurality of zones.

Numerous other advantages and features of the present disclosure will become readily apparent from the following detailed description, the accompanying drawings, and the appended claims.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

DETAILED DESCRIPTION

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Figure 1:
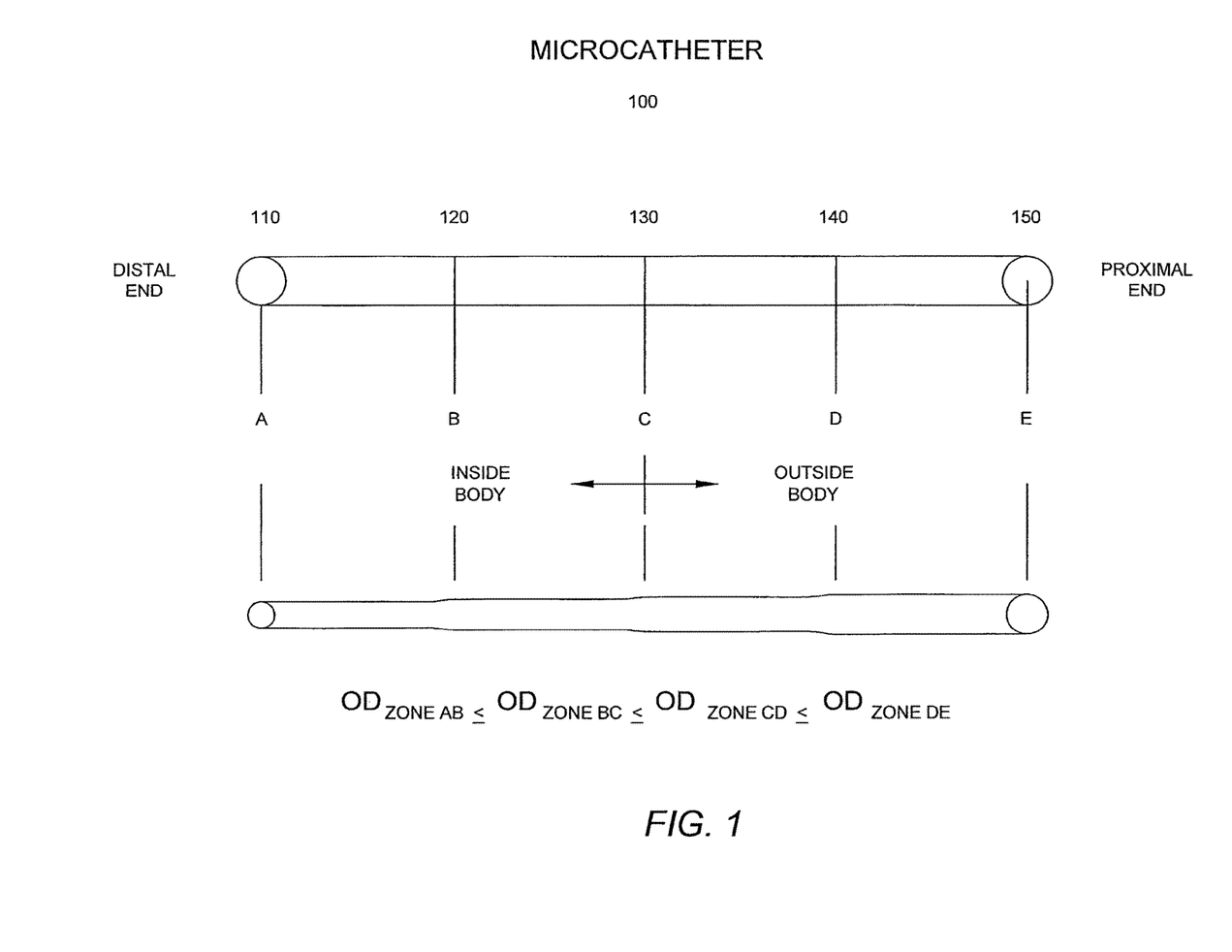
FIG. 1 is a schematic illustration of a microcatheter in accordance with one embodiment.

FIG. 1 illustrates a notional schematic of a microcatheter according to an embodiment of the present disclosure. The microcatheter 100 is designed along standard neuroendovascular microcatheter platforms with a generally tubular body to allow for the delivery of, e.g., detachable coil systems, particulate matter injections, as well as liquid injection and infusions in either a transient and/or in situ continuous manner. The microcatheter 100 has a distal end 110, which is also marked as A, a proximal end 150, which is also marked as E, and a transition portion. The transition portion of the microcatheter 100 includes four distinct zones from 110 to 120 is zone AB, from 120 to 130 is zone BC, from 130 to 140 is zone CD, and from 140 to 150 is zone DE. In one embodiment, zone AB and zone BC are usually disposed inside a body, while zone CD and zone DE are usually disposed outside the body.

In an embodiment, the tubular body of the microcatheter 100 has an increasing outer diameter ("OD") in the direction from the distal end to the proximal end. For example, the outer diameter of zone AB is no greater than the outer diameter of zone BC, the outer diameter of zone BC is no greater than the outer diameter of zone CD, the outer diameter of zone CD is no greater than the outer diameter of zone DE.

In another embodiment, more than four zones are employed. In another embodiment, fewer than four zones are employed. In another embodiment, more than two zones are placed inside the body. In yet another embodiment, fewer than two zones are placed inside the body.

In one embodiment, the transition in outer diameter between any two abutting zones is a step change. In another embodiment, the transition in outer diameter between any two abutting zones is a gradual change. In another embodiment, the transition in outer diameter between any two abutting zones is a taper change. In another embodiment, the transition in outer diameter between any two abutting zones is a chamfer change. In another embodiment, the transition in outer diameter between any two abutting zones is a fillet change. One of skill in the art will readily understand that the current disclosure encompasses situations where more than one type of transition occurs along the length of a microcatheter such as, for a non-limiting example, a step change occurs between a first two abutting zones and a tapering change occurs between a second two abutting zones.

One advantage of the microcatheter described herein is that the substantially increased proximal outer diameter of the microcatheter and microcatheter extension increases the stability of the overall microcatheter system.

In one embodiment, the overall length of the microcatheter 100 is 150 cm and may optionally include one or two distal radio-opaque markers for visualization with detachable coil deployment. In one embodiment, the microcatheter 100 employs a nitinol braiding system throughout the entire length which enables improved stability. In one embodiment, the inner diameter of the microcatheter 100 remains constant at 0.4138 mm throughout the entire length of the microcatheter 100. In another embodiment, the inner diameter of the microcatheter 100 remains constant at approximately 0.4 mm.

In one embodiment, zone AB is 30 cm in length and 0.57 mm in outer diameter (or 1.7 Fr); zone BC is 15 cm in length, and 0.73 mm (or 2.2 Fr) in outer diameter; zone CD is 15 cm in length, and 1.17 mm (or 3.5 Fr) in outer diameter; zone DE is 90 cm in length, and 1.33 mm (or 4 Fr) in outer diameter.

As would be apparent to one of ordinary skill in the art, the exemplary length or lengths listed above for any one or more zone may be different without departing from the spirit and intent of the present disclosure. Similarly, the exemplary inner diameter may be different without departing from the spirit and intent of the present disclosure. Likewise, the exemplary outer diameters listed above for any one or more zone may be different without departing from the spirit and intent of the present disclosure.

Figure 2:
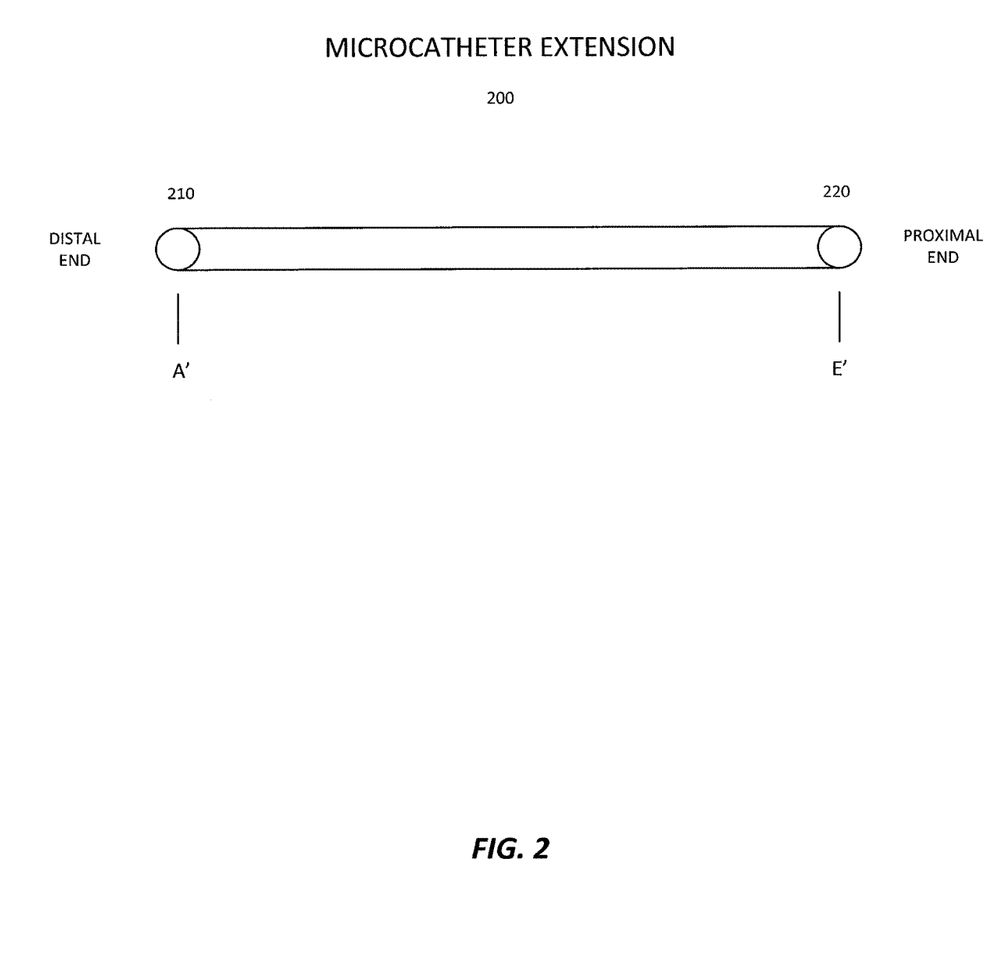
FIG. 2 is a schematic illustration of a microcatheter extension in accordance with one embodiment.
Figure 3:
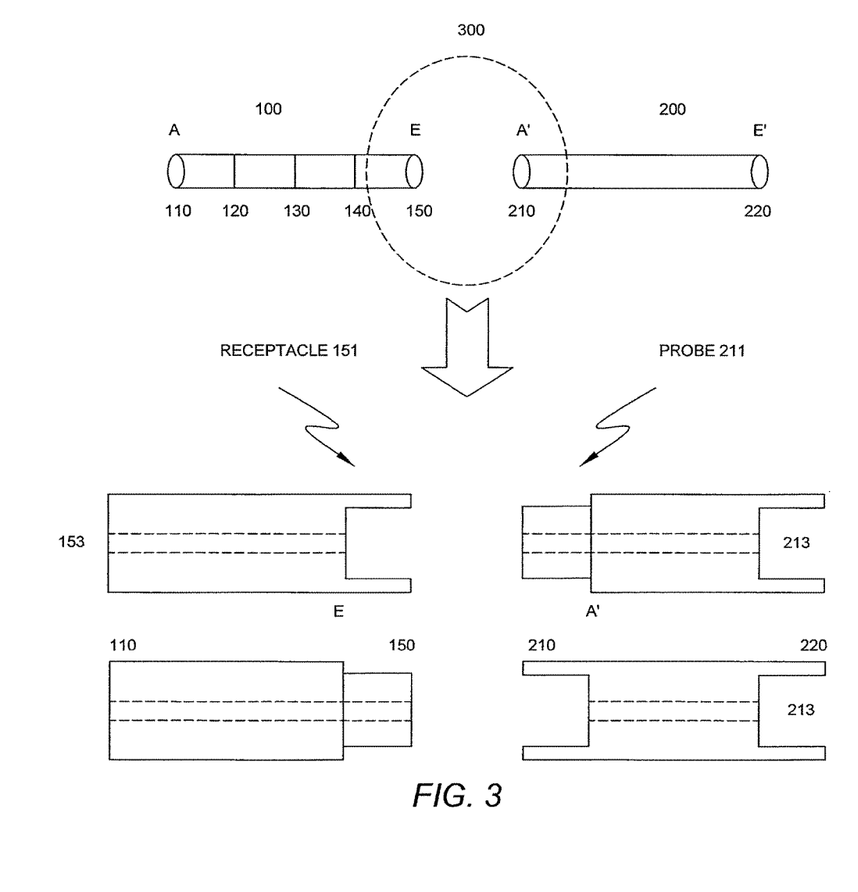
FIG. 3 is a schematic illustration of the connection between a microcatheter and a microcatheter extension in accordance with one embodiment.
Figure 4:
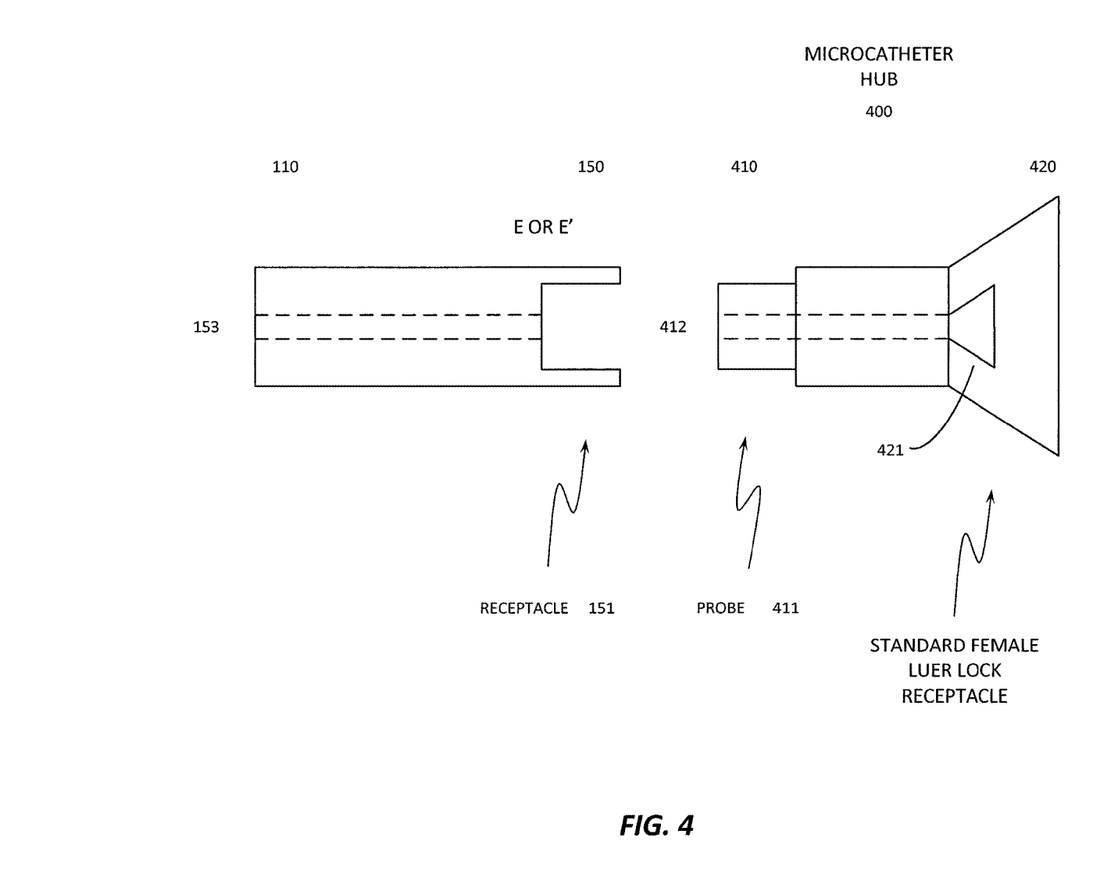
FIG. 4 is a schematic illustration of a connection between a microcatheter and a microcatheter hub, or the connection between a microcatheter extension and a microcatheter hub in accordance with one embodiment.

In one embodiment, the proximal end 150 (E) of the microcatheter 100 contains a female portion of a unique joining mechanism (e.g., female internal Luer lock mechanism) by which either the microcatheter extension 200 in FIG. 2 or FIG. 3 or the detachable/attachable microcatheter hub 400 in FIG. 4 may be attached and/or detached. This unique design allows the microcatheter 100 to be utilized as a standard microcatheter or as an exchange length microcatheter. In another embodiment, the proximal end 150 (E) of the microcatheter 100 contains a unique male portion of the unique joining mechanism (e.g., male internal Luer lock mechanism) by which either the microcatheter extension 200 or the detachable/attachable microcatheter hub 400, each having a unique female internal Luer lock mechanism, may be attached and/or detached. The internal Luer lock mechanism allows the microcatheter extension 200 to be coupled to the microcatheter 100 in such a manner as to allow the safe and effective removal of commonly employed guide catheter from the parent artery, allowing for continued treatment through the microcatheter 100 for a prolonged manner and decreasing the risk associated with thromboembolic complications.

FIG. 2 illustrates a notional schematic of a microcatheter extension 200 according to an embodiment of the present disclosure. In an embodiment, this microcatheter extension 200 is similar in material and configuration in terms of inner diameter and outer diameter as zone DE of the microcatheter 100 shown in FIG. 1. In one embodiment, the overall length of the microcatheter extension 200 from 210 to 220, or A'E' is 150 cm, the inner diameter 213 throughout remains the same as the inner diameter of the microcatheter 100, which, in an embodiment, may be 0.4138 mm, and the outer diameter throughout remains the same as the outer diameter of zone DE, which is 1.33 mm. Other lengths and diameters of the microcatheter extension 200 are contemplated in keeping with the principles of the present disclosure.

FIG. 3 illustrates a notional schematic of the internal Luer lock mechanism connection 300 according to an embodiment of the present disclosure. In one embodiment, at the distal end 210 of the microcatheter extension 200 (A') is a unique male internal Luer lock mechanism 211 which allows for connection to the proximal end 150 of either the microcatheter 100 or another microcatheter extension 200. At the proximal end 150 of the microcatheter 100 is a unique female internal Luer lock mechanism 151. At the proximal end 220 of the microcatheter extension (E') is a unique female internal Luer lock mechanism which is identical in design to the mechanism found at the proximal end 150 of the microcatheter 100 (as shown at E in FIG. 3). This allows for connection with either an additional microcatheter extension 200 or detachable/attachable microcatheter hub 400 (FIG. 4). Internal diameter 153 is constant as described above. In an embodiment, the internal Luer lock mechanism 300 (e.g., receptacle 151 and probe 211) is designed so that, preferably, the internal passageways/diameters 153 and 211 are aligned when the microcatheter 100 and extension 200 are joined.

In an alternate embodiment, the respective male and female portions are swapped between the connecting components. For example, at the distal end of the microcatheter extension 210 (A') is a unique female internal Luer Lock mechanism which allows for connection to the proximal end 150 of either the microcatheter 100 or microcatheter extension 200. At the proximal end 220 of the microcatheter extension 200 (E') is a unique male internal Luer lock mechanism which is identical in design to the mechanism found at the proximal end 150 of the microcatheter 100.

One advantage of the microcatheters described herein is that the unique Luer lock mechanism permits attachment and detachment of the microcatheter extension in tandem and/or with a microcatheter hub. Effectively creating an extended microcatheter with a detachable hub permits the safe and effective removal of a standard guiding catheter in standard exchange technique. This also allows the microcatheter described herein to be used as a standard endovascular/neuroendovascular microcatheter for standard, commonly employed procedures as well as increased utility when coupled with other components of the system.

FIG. 4 illustrates a notional schematic of the internal Luer lock connection between a microcatheter 100, or a microcatheter extension 200, and a microcatheter hub 400 having a distal end 410 and a proximal end 420, according to an embodiment of the present disclosure. In an embodiment, the microcatheter hub 400 is similar in design and composition to the standard endovascular microcatheter proximal aspect; a standard female Luer lock mechanism permits connection with standard Luer lock syringes, connectors, and intravenous tubing. In an embodiment, the detachable/attachable microcatheter hub 400 distal aspect 411 is unique in that it possess a unique male internal Luer lock system which permits connection to either the proximal aspect 151 of either the microcatheter 100 or microcatheter extension 200. The proximal end 420 of themicrocatheter hub 400 is designed on a similar platform to the standard microcatheter hubs, e.g., having a standard Luer lock receptacle 421, which allows for connection with standard Luer lock syringes, additional adapters such as three-way connectors and rotating hemostatic valves, as well as intravenous tubing to permit passage of detachable coil systems, particular matter, continuous liquid infusions, as well as syringe injections. Internal diameter 412 may be constant throughout as described above. In an embodiment, the internal Luer lock mechanism shown in FIG. 4 (e.g., receptacle 151 and probe 411) is designed so that, preferably, the internal passageways/diameters 153 and 412 are aligned when the microcatheter 100 and hub 400 are joined.

In another embodiment, the detachable/attachable microcatheter hub 400 distal aspect is unique in that it possess a unique female internal Luer lock system which permits connection to either the proximal aspect 150 of either the microcatheter 100 or microcatheter extension 200. The ability to attach or detach the detachable/attachable microcatheter hub 400 permits the use of the microcatheter 100 as either a standard endovascular, or neuroendovascular microcatheter and/or as an exchange length microcatheter. The detachable/attachable microcatheter hub 400 is compatible with Dimethyl-Sulfoxide, and possess a pressure rating identical to the standard endovascular or neuroendovascular microcatheters. In a further embodiment, the connection between the microcatheter 100 or microcatheter extension 200 and microcatheter hub 400 may be a standard Luer lock-type arrangement.

In certain embodiments, microcatheter 100 and microcatheter extension 200 and microcatheter hub 400 are all compatible with each of the following: dimethyl sulfoxide (DMSO), Onyx liquid embolic agent (LES) 18, Onyx LES 20, Onyx LES 34, Onyx LES HD 500, ethiodized oil, TRUFILL liquid embolic system (n-butyl cyanoacralate (nBCA))

One advantage of the microcatheters described herein is the improved performance of the microcatheters and increased safety with the exchange technique.

Figure 5A:
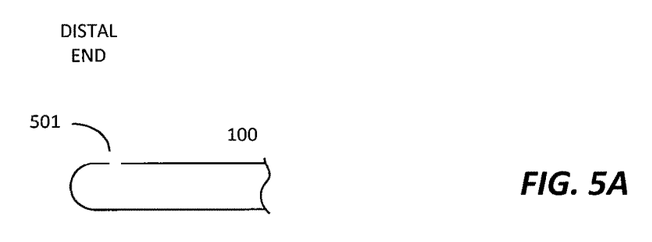
FIGS. 5A to 5C each illustrate a separate notional embodiment of a distal end of a microcatheter.
Figure 5B:
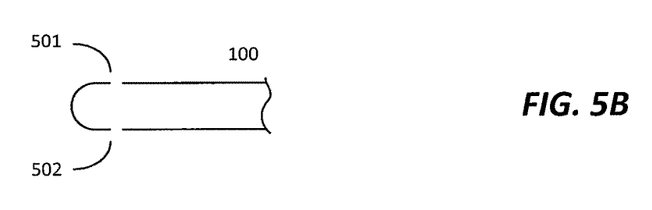
Figure 5C:
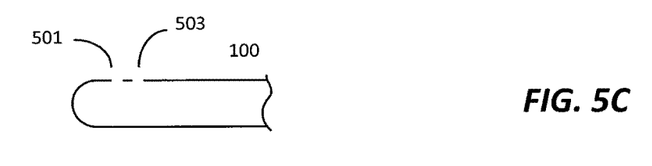

FIGS. 5A to 5C each illustrate a separate notional embodiment of a distal end of a microcatheter. FIG. 5A illustrates a notional microcatheter 100, as described above, showing an embodiment where the distal end of microcatheter 100 is closed and there is a hole 501 (slit, perforation, etc.) in a sidewall of the microcatheter. FIG. 5B illustrates a notional microcatheter 100, as described above, showing an embodiment where the distal end of microcatheter 100 is closed and there is a hole 501 and a hole 502 (slit, perforation, etc.) in a sidewall of the microcatheter. In a further embodiment, the holes 501 and 502 oppose each other. FIG. 5C illustrates a notional microcatheter 100, as described above, showing an embodiment where the distal end of microcatheter 100 is closed and there is a hole 501 and a hole 503 (slit, perforation, etc.) in a sidewall of the microcatheter. In a further embodiment, the holes 501 and 503 are adjacent each other. In a still further embodiment, holes 501 and 503 are aligned with each other. Other embodiments include multiple holes near the distal end of the microcatheter 100. The hole or holes near the distal end of microcatheter 100 allow for fluid ingress/egress as required by the particular use the microcatheter performs. Those of skill in the art will readily understand that the present disclosure is not limited to the embodiments shown in FIGS. 5A to 5C but may also encompass any number of holes near the distal end of the microcatheter. Further embodiments include one or more holes in a sidewall of the microcatheter as well as a hole in the distal end of the microcatheter as shown, e.g., in FIG. 1. Still further embodiments require the one or more holes in the distal end of the microcatheter 100 to be within 2 cm of the distal end. Yet further embodiments require that the one or more holes in the distal end of the microcatheter 100 to be approximately 2 cm from the distal end.

In further embodiments, microcatheters, microcatheter extensions, and/or microcatheter hubs, each as described above, may be employed in any one or more of the following uses and/or procedures:

1. in dwelling microcatheter for the treatment of arterial vasospasm;
2. in dwelling microcatheter for intra-arterial infusion of vasoactive substance/chemical angioplasty;
3. in dwelling microcatheter for the treatment of arterial occlusion, thrombosis, stenosis;
4. in dwelling microcatheter for intra-arterial tPA administration;
5. in dwelling microcatheter for the treatment of venous occlusion, thrombosis, stenosis;
6. in dwelling microcatheter for intra-venous tPA administration;
7. delivery and placement of endovascular/intracranial stent;
8. delivery and placement of endovascular/intracranial thrombectomy device;
9. intracranial thrombectomy via aspiration and/or delivery of thrombectomy device;
10. delivery and placement of embolic particles such as polyvinyl alcohol (PVA), embospheres, gel foam, and other particulate material;
11. delivery and placement of intra-saccular embolization products such as aneurysm coils and other future devices;
12. delivery and placement of intracranial balloons for angioplasty;
13. delivery and placement of intracranial stents for angioplasty/stenting in atherosclerosis or occlusive disease;
14. delivery and placement of intracranial stents for aneurysm bridging;
15. delivery and placement of intracranial stents for vascular remodeling and flow diversion;
16. intra-arterial infusion of oncological/chemotherapeutic agents;
17. intra-arterial infusion of antibiotic/antifungal agents;
18. treatment of head, neck, and brain malignancies;
19. treatment of head, neck, brain infections;
20. embolization for brain aneurysms, brain tumors, arteriovenous malformations and fistulas, head and neck tumors, epistaxis and uncontrolled bleeding of the head and neck for any underlying etiology;
21. stent placement for cerebrovascular insufficiency and stroke, vasospasm, aneurysm bridging, vascular remodeling, venous outflow insufficiency;
22. infusion for vasospasm, thrombolysis, stroke, venous occlusion, intracranial malignancy, head and neck malignancy;
23. exchange system to allow introduction/removal of additional guide catheters and intermediary catheters;
24. support system to facilitate coaxial advancement of additional catheters.

In further embodiments, microcatheters, microcatheter extensions, and/or microcatheter hubs, as described above, employed for any one or more of the above uses/procedures may be employed in peripheral vascular situations.

Although the subject matter has been described in terms of exemplary embodiments, it is not limited thereto. Rather, the appended claims should be construed broadly, to include other variants and embodiments, which may be made by those skilled in the art.

What is claimed is:

1. A microcatheter system comprising:
a microcatheter having a distal end and a proximal end, a plurality of zones, a passage, and a first receptacle, wherein an internal diameter of the passage is constant throughout the plurality of zones, and wherein each zone has an outside diameter constant across the respective zone that is progressively greater than an immediately adjacent and more distal zone, wherein the proximal end of said microcatheter is configured with the first receptacle receiving a first probe connecting a first microcatheter extension or a microcatheter hub to said microcatheter, and wherein an outside diameter of the first receptacle is no greater than a largest diameter of the zones in the plurality of zones; and
said first microcatheter extension having a distal end and a proximal end, a second passage, a first portion, and the first probe, wherein an internal diameter of the second passage is constant throughout the first portion and the first probe, and wherein an outside diameter of the first portion is constant throughout, and wherein the distal end of said first microcatheter extension is configured with the first probe to be received by the first receptacle of the proximal end of said microcatheter, and wherein an outside diameter of the first probe is constant and less than an internal diameter of the first receptacle,
wherein the internal diameter of the passage of the plurality of zones of said microcatheter is the same as the internal diameter of the second passage of said first microcatheter extension,
wherein an outside diameter of said first portion of the first microcatheter extension is the same as the outside diameter of the largest diameter of the zones in the plurality of zones, and
wherein the distal end of said microcatheter includes a perforation through a sidewall of the microcatheter.

2. The microcatheter system of claim 1 wherein said microcatheter includes a perforation through an end wall of the distal end of the microcatheter.

3. The microcatheter system of claim 1 wherein a portion of the distal end of said microcatheter includes a plurality of perforations through the sidewall of the microcatheter.

4. The microcatheter system of claim 3 wherein said portion of the distal end encompasses a predetermined linear distance along a longitudinal axis of said microcatheter.

5. The microcatheter system of claim 4 wherein said predetermined linear distance is approximately 2 cm.

6. The microcatheter system of claim 5 wherein said predetermined linear distance is measured from an end wall of the distal end of the microcatheter.

7. The microcatheter system of claim 4 wherein said predetermined linear distance is no greater than 2 cm.

8. The microcatheter system of claim 7 wherein said predetermined linear distance is measured from an end wall of the distal end of the microcatheter.

9. A microcatheter system comprising:
a microcatheter having a distal end and a proximal end, a passage, a plurality of zones and a first probe, wherein an internal diameter of the passage is constant throughout, and wherein each zone has an outside diameter constant across the respective zone that is progressively greater than an immediately adjacent and more distal zone, wherein the proximal end of said microcatheter is configured as the first probe connecting to a first receptacle of a first microcatheter extension or a microcatheter hub, and wherein an outside diameter of the first probe is constant and less than an internal diameter of the first receptacle; and said first microcatheter extension having a distal end and a proximal end, a second passage, a first portion, and the first receptacle, wherein an internal diameter of the second passage is constant throughout, and wherein an outside diameter of the first portion is constant throughout, and wherein the distal end of said first microcatheter extension is configured as the first receptacle to receive the first probe of the proximal end of said microcatheter, and wherein an outside diameter of the first receptacle is no greater than a largest diameter of the zones in the plurality of zones, wherein the internal diameter of the passage of said microcatheter is the same as the internal diameter of the second passage of said first microcatheter extension, wherein an outside diameter of the first portion of said first microcatheter extension is the same as the outside diameter of the largest diameter of the zones in the plurality of zones, and wherein the distal end of said microcatheter includes a perforation through a sidewall of the microcatheter.

10. The microcatheter system of claim 9 wherein said microcatheter includes a perforation through an end wall of the distal end of the microcatheter.

11. The microcatheter system of claim 9 wherein a portion of the distal end of said microcatheter includes a plurality of perforations through the sidewall of the microcatheter.

12. The microcatheter system of claim 11 wherein said portion of the distal end encompasses a predetermined linear distance along a longitudinal axis of said microcatheter.

13. The microcatheter system of claim 12 wherein said predetermined linear distance is approximately 2 cm.

14. The microcatheter system of claim 13 wherein said predetermined linear distance is measured from an end wall of the distal end of the microcatheter.

15. The microcatheter system of claim 12 wherein said predetermined linear distance is no greater than 2 cm.

16. The microcatheter system of claim 15 wherein said predetermined linear distance is measured from an end wall of the distal end of the microcatheter.

17. A method of using a microcatheter comprising:

providing a microcatheter having a distal end and a proximal end, a plurality of zones, a passage, and a first receptacle wherein an internal diameter of the passage is constant throughout the plurality of zones, and wherein each zone has an outside diameter constant across the respective zone that is progressively greater than an immediately adjacent and more distal zone, wherein the proximal end of said microcatheter is configured with the first receptacle receiving a first probe connecting a first microcatheter extension or a microcatheter hub to said microcatheter, and wherein an outside diameter of the first receptacle is no greater than a largest diameter of the zones in the plurality of zones; and attaching said first microcatheter extension to said first microcatheter, wherein said first microcatheter extension has a distal end and a proximal end, a second passage, a first portion, and the first probe, wherein an internal diameter of the second passage is constant throughout the first portion and the first probe, and wherein an outside diameter of the first portion is constant throughout, and wherein the distal end of said first microcatheter extension is configured with the first probe to be received by the first receptacle of the proximal end of said microcatheter, and wherein an outside diameter of the first probe is constant and less than an internal diameter of the first receptacle, wherein the internal diameter of the passage of the plurality of zones of said microcatheter is the same as the internal diameter of the second passage of said first microcatheter extension, and wherein an outside diameter of said first portion of the first microcatheter extension is the same as the outside diameter of the largest diameter of the zones in the plurality of zones.

18. The method of claim 17 wherein the distal end of the microcatheter includes a perforation through a sidewall of the microcatheter.

19. The method of claim 18 wherein a portion of the distal end of said microcatheter includes a plurality of perforations through the sidewall of the microcatheter.

20. The method of claim 19 wherein the portion of the distal end encompasses a predetermined linear distance along a longitudinal axis of said microcatheter.

* * * * *